(12) United States Patent
Verma et al.

(10) Patent No.: US 12,280,071 B2
(45) Date of Patent: Apr. 22, 2025

(54) SELF-ASSEMBLED NANO-FIBERS AS HEMOSTATIC AGENT

(71) Applicant: NATIONAL INSTITUTE OF TECHNOLOGY ROURKELA, Rourkela (IN)

(72) Inventors: Devendra Verma, Rourkela (IN); Sabir Hossain, Burdwan Sadar (IN)

(73) Assignee: NATIONAL INSTITUTE OF TECHNOLOGY ROURKELA, Rourkela (IN)

( * ) Notice: Subject to any disclaimer, the term of this patent is extended or adjusted under 35 U.S.C. 154(b) by 702 days.

(21) Appl. No.: 17/604,264

(22) PCT Filed: Apr. 17, 2020

(86) PCT No.: PCT/IN2020/050364
§ 371 (c)(1),
(2) Date: Oct. 15, 2021

(87) PCT Pub. No.: WO2020/213012
PCT Pub. Date: Oct. 22, 2020

(65) Prior Publication Data
US 2022/0193115 A1    Jun. 23, 2022

(30) Foreign Application Priority Data
Apr. 18, 2019  (IN) .............................. 201931015575

(51) Int. Cl.
| | | |
|---|---|---|
| *A61K 31/722* | (2006.01) | |
| *A61K 9/00* | (2006.01) | |
| *A61K 9/70* | (2006.01) | |
| *A61P 7/04* | (2006.01) | |

(52) U.S. Cl.
CPC .......... *A61K 31/722* (2013.01); *A61K 9/0092* (2013.01); *A61K 9/7007* (2013.01); *A61P 7/04* (2018.01)

(58) Field of Classification Search
None
See application file for complete search history.

(56) References Cited

U.S. PATENT DOCUMENTS

2003/0134120 A1    7/2003    Kim et al.

FOREIGN PATENT DOCUMENTS

| CN | 101992029 A | 3/2011 |
|---|---|---|
| CN | 103505758 A | 1/2014 |
| CN | 108342111 A | 7/2018 |

OTHER PUBLICATIONS

Aldridge, Susan, et al., "Recombinant Thrombin Approved," Nature Publishing Group, downloaded from http://www.nature.com/naturebiotechnology, 2008.
Anal, A.K. et al., "Preparation and characterization of nanoparticles formed by chitosan-caseinate interactions," Colloids and Surfaces V: Biointerfaces vol. 64, No. 1, pp. 104-110, Jun. 15, 2008.
Biranje, Santosh et al., "Porous electrospun Casein/PVA nanofibrous mat for its potential application as wound dressing material," Journal of Porous Materials, vol. 26, No. 1, pp. 29-40, 2019.
Cheng, Christine M., et al., "A Review of Three Stand-Along Topical Thrombins for Surgical Hemostasis," Clinical Therapeutics, vol. 31, pp. 32-41, No. 1, 2009.
Delgado, Angel, V., "A Novel Biologic Hemostatic Dressing (Fibrin Patch) Reduces Blood Loss and Reuscitation Volume and Improves Survival in Hypothermic, Coagulopathic Swing with Grade V Liver Injury," The Journal of Trauma Injury, Infection, and Critical Care, vol. 64, No. 1, pp. 75-80, 2008.
Heiskell, L., et al., "Blood Clotters," Police Law Enforcement Solutions magazine, Aug. 1, 2004.
International Search Report mailed Jun. 23, 2020 in International Application No. PCT/IN2020/050364.
Mirzakhanian, Zeinab, et al., "Synthesis and characterization of fast-swelling porous superabsorbent hydrogel based on starch as a hemostatic agent," Journal of Biomaterials Science, Polymer Edition, vol. 26, No. 18, pp. 1439-1451, 2015.
Sims, Kyle F., et al., "Management of External Hemorrhage in Tactical Combat Casualty Care The Adjunctive Use of XStat Compressed Hemostatic Sponges. TCCC Guidelines: Change 15-03," Journal of Special Operations Medicine, vol. 15, edition 1, Spring 2016.
Written Opinion mailed Jun. 23, 2020 in International Application No. PCT/IN2020/050364.

*Primary Examiner* — Layla D Berry
(74) *Attorney, Agent, or Firm* — Knobbe, Martens, Olson & Bear, LLP

(57) ABSTRACT

A composition has a polyanionic component comprising casein or derivatives thereof, and a polycationic component, which includes chitosan or derivatives thereof. The composition is in the form of nanofibers having a diameter in a range of 20-200 nm. Also disclosed is a process for preparing the composition and a hemostatic article with the composition. A method for inhibiting loss of blood from a hemorrhaging site involves use of the composition and the hemostatic article.

16 Claims, 6 Drawing Sheets

SELF-ASSEMBLED NANO-FIBERS AS HEMOSTATIC AGENT

PRIORITY AND CROSS REFERENCE TO RELATED APPLICATIONS

This application is the U.S. National Phase under 35. U.S.C. § 371 of International Application PCT/IN2020/050364, filed Apr. 17, 2020, designating the U.S. and published in English as WO 2020/213012 A1 on Oct. 22, 2020, which claims the benefit of Indian Patent Application number 201931015575, filed Apr. 18, 2019. Any and all applications for which a foreign or a domestic priority is claimed is/are identified in the Application Data Sheet filed herewith and is/are hereby incorporated by reference in their entireties under 37 C.F.R. § 1.57.

TECHNICAL FIELD

The subject matter described herein, in general, relates to the field of polyelectrolytes, and particularly, relates to a composition for inhibiting excessive blood-loss from a haemorrhaging site.

BACKGROUND OF INVENTION

Excessive blood loss is one of the major causes of death for soldiers as well as for civilians. Other than major organ injuries, many people die because of excessive blood loss only. According to the doctors almost 80% of the military personnels die within half an hour of the injury due to massive blood loss. Same is the case with the civilians as well. Approximately 50% of the accident victims succumb to death before receiving adequate treatment just because of huge blood loss (Heiskell et al., Blood clotters, Police Magazine, 2004). Therefore, research work promoting inhibition of excessive blood loss in less time comes as a boon to address this pertinent problem.

Blood has its own complex coagulation process, composed of distinctive extrinsic and intrinsic pathways. So, whenever there is small cut, blood clots by itself and prevents further bleeding, but in case of deep cuts, blood does not clot on its own. Owing to this problem, there should be an external component that can assist in the self-clotting mechanism of the blood and promote rapid hemostasis leading to prevention of blood-loss.

Several materials in different forms have been investigated to control the hemorrhage effectively. In fact, variety of materials are already available in the market, but most of these have their own flaws in terms of their efficiency and price. For example, QuickClot™ induces rise in temperature upon application, Hemcon™ is very costly, and XStat can cause foreign body reaction if it is left inside the body. Moreover, high cost of most of these clotting agents is another drawback which prevents their widespread use.

Absorptive biomaterials impart partial hemostasis simply by absorption of blood and exudates. Cellulose, oxidized cellulose, oxidized regenerated cellulose and starch-based bandages belong to this category. Various products based on absorption mechanism have been developed, such as HaemoCer™ Plus™, Arista™, PerClot™, and Starsil Hemostatic Powders™. Starch-based fast-swelling porous superabsorbent hydrogel (FSPSH) was also reported (J Biomater Sci Polym Ed. 2015; 26:1439-1451). X-Stat™ by RevMedx™ is based on absorptive mechanism (J Spec Oper Med. 2016; 16:19-28). It has been developed for deep wounds, such as gun-shot wounds. However, as it is based on wood pulp, it may cause severe foreign body reaction if left inside the body.

Since fibrin plays a crucial role in the formation of a stable clot, fibrin, fibrinogen, and thrombin have been used for hemostatic effect. Fibrin based dressings have exhibited superior hemostatic performance compared to absorptive dressings (J Trauma Inj Infect Crit Care. 2008; 64:75-80). Products like TachoComb™ and TachoSil™ are few examples of fibrin-based hemostatic agents.

In recent years, efforts have also been made to develop recombinant versions of such coagulation proteins (Clin Ther. 2009; 31:32-41). One just example is clinically approved Recothrom™, which is a fully recombinant human thrombin (Nat Biotechnol. 2008; 26:250-250). Fibrin dressings have great potential for reducing mortality.

Considering the present scenario, there are challenges associated with cost effective clotting agents that are easily available. Moreover, fibrin sourced from an animal (bovine, porcine) or human pooled blood pose an additional risk of immunogenicity and viral contamination. In addition, since the reconstitution is required before application, these bandages cannot be used in case of emergency.

Therefore, there is an urgent need for a hemorrhage controlling agent that is cost-effective, easily available, has lesser risk of immunogenicity, has no viral contamination, and can be used in emergency situations.

SUMMARY OF THE INVENTION

In an aspect of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm.

In a second aspect of the present disclosure, there is provided a process for preparing a composition comprising: (i) a polyanionic component comprising casein or derivatives thereof; and (ii) a polycationic component comprising chitosan or derivatives thereof, wherein the composition is in form of nanofibers having a diameter in a range of 20-200 nm, said process comprising: (a) contacting a first aqueous solution of the polyanionic component comprising casein or derivatives thereof with a second aqueous solution of the polycationic component comprising chitosan or derivatives thereof, to obtain an aqueous mixture; (b) processing the aqueous mixture to obtain suspended particles; (c) contacting the suspended particles with a desolvating agent, to obtain a suspension; and (d) drying the suspension to obtain the composition.

In a third aspect of the present disclosure, there is provided a hemostatic article comprising a composition, said composition comprising: (a) a polyanionic component comprising casein or derivatives thereof; and (b) a polycationic component comprising chitosan or derivatives thereof, wherein the composition is in form of nanofibers having a diameter in a range of 20-200 nm.

In a fourth aspect of the present disclosure, there is provided a method for inhibiting loss of blood from a haemorrhaging site, said method comprising: (a) obtaining the composition as described herein or the hemostatic article as described herein; and (b) applying the composition to a haemorrhaging site for inhibiting loss of blood from the haemorrhaging site.

In a fifth aspect of the present disclosure, there is provided a use of the composition comprising: (i) a polyanionic component comprising casein or derivatives thereof; and (ii) a polyanionic component comprising chitosan or derivatives thereof, wherein the composition is in form of nanofibers having a diameter in a range of 20-200 nm for inhibiting loss of blood from a haemorrhaging site.

In a sixth aspect of the present disclosure, there is provided a use of the hemostatic article comprising a composition, said composition comprising: (i) a polyanionic component comprising casein or derivatives thereof; and (ii) a polycationic component comprising chitosan or derivatives thereof, wherein the composition is in form of nanofibers having a diameter in a range of 20-200 nm for inhibiting loss of blood from a haemorrhaging site These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. The same numbers are used throughout the specification referring to drawings like features and components of different drawings.

DETAILED DESCRIPTION OF THE INVENTION

Figure 1:
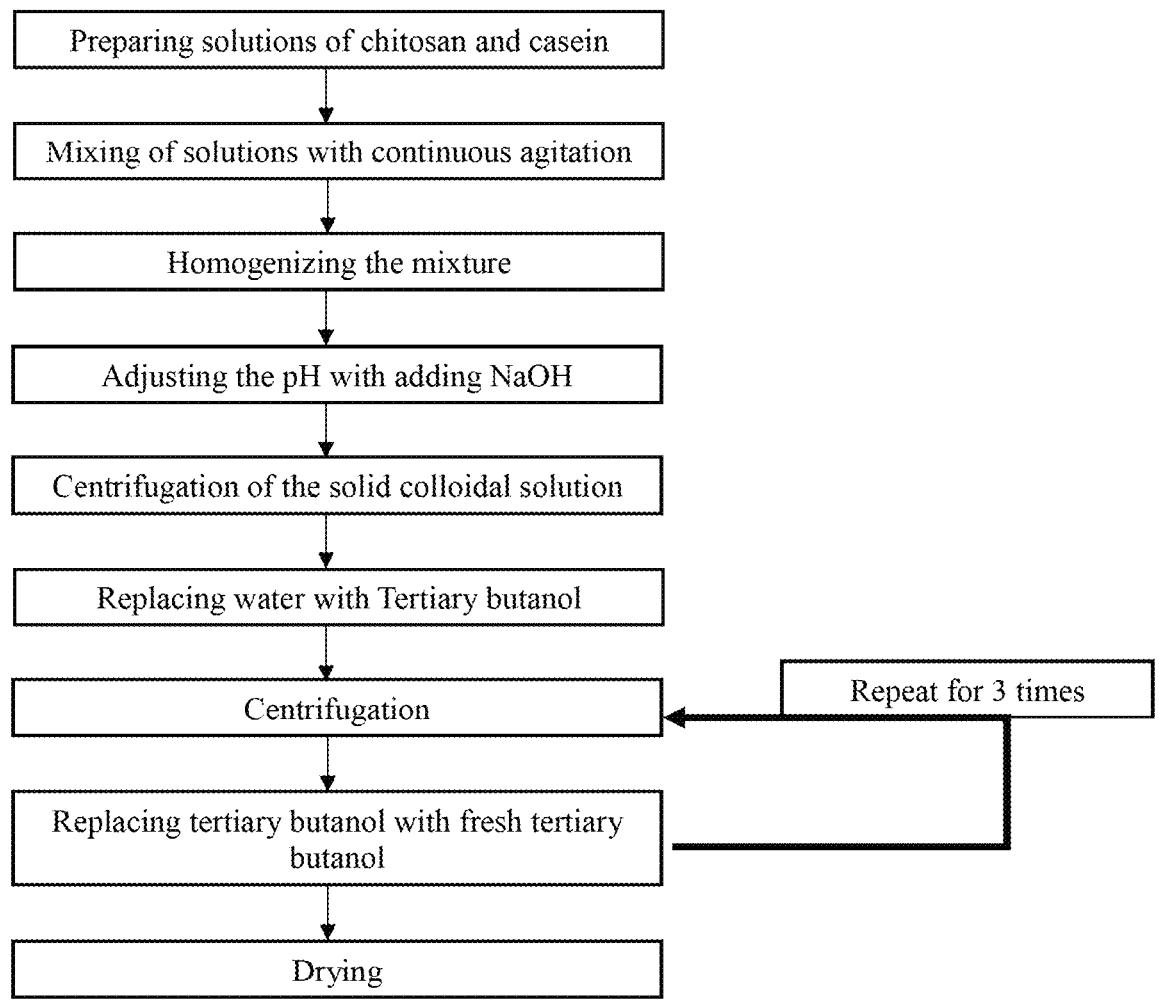
FIG. 1 illustrates the process steps for preparing the composition, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles 'a', 'an' and 'the' are used to refer to one or more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise" and variations such as "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a diameter range of 20-200, should be construed to include 30 and 76, and also include sub-ranges such as 35-93, 21-64, 35-90 and so on.

The term "at least one" is used to mean one or more and thus includes individual components as well as mixtures/combinations.

The term "nano-fibers" depicts the fibers with a diameter in the nanometer range.

The term "polyelectrolyte complex" or "PEC" depicts the complex formed between two polymers, in which at least one polymer is polycationic and the other polymer is polyanionic.

The term "wound site" or "wound" depicts any site on a body of any animal or human that is wounded or has undergone a physical trauma leading to loss of blood. The present disclosure intends to cover the application of the composition (nanofibers) as described herein on the wound site of any animal or human or any living organism which requires any sort of intervention in order to stop the blood loss.

The term "hemocompatible" depicts the compatibility to the red blood cells or blood with any substrate or in the instant case with the PEC.

The terms "antimicrobial agent, growth factor, anti-inflammatory agent, anti-histamine, a compound containing copper or silver ions" are used to depict well-known components of the broad category known to a person skilled in the art.

The term "haemorrhaging" refers to excessive loss of blood. A site is referred to as a haemorrhaging site if excessive loss of blood is taking place on the site.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

In order to address the problems that are associated with the existing hemostatic agents, the present disclosure provides a composition which is a nanofibrous polyelectrolyte complex comprising casein and chitosan. The composition is a self-assembling reconstituted nanofibrous polyelectrolyte complex which promotes efficient hemostasis. As per the present disclosure, the composition (nanofibrous PEC) has been fabricated through the self-assembly process that has been determined to be a suitable hemostatic agent. Nanofibers are generally fabricated using phase separation, self-assembly, and electrospinning. Among these techniques, electrospinning has become the most preferred method as diverse array of polymers can be used to make nano-fibers. However, the entangled fibrous structure of the electrospun mat limits their use in powder form for hemostatic application. Another challenge with electrospinning method is achieving high throughput. In the present disclosure short nanofibers with varying surface charges have been fabricated using self-assembly method. This method allows production of nanofibrous powder, which can be easily scaled up for commercial purpose.

The present disclosure provides the development of a hemorrhage controlling agent that is composed of a polycationic polymer and a protein (in polyanionic form) that leads to the formation of nanofibers with average fiber diameter of less than 200 nanometer, wherein these nanofibers have been developed through a self-assembly method that gives a very high throughput and is easy to transform into industrial production. The composition as disclosed in the present disclosure has several applications, namely, in controlling hemorrhage cause due to any kind of accidents, surgery, or body's own physiology. The composition is also very effective in cases of gunshots, knife stabs, clinical wounds, post-operative incisions, wound dressing etc. directly as powder, patch, gel or bandage. Other than that, the composition can be used as a wound dressing material, for coating of medical implants and devices and in conjunction with bandages.

The composition as disclosed in the present disclosure provides a nano-fibrous powder with fiber diameter in a range of 20-200 nm. It has the ability to clot the blood within 20 seconds for fatal injuries and almost instantaneous stoppage of bleeding in surface lacerations, aberration, incision etc. The present disclosure also provides the fabrication process of aforesaid biomaterials that has been done through self-assembly method.

The disclosed composition (nano-fibrous polyelectrolyte complex) can be fabricated by preparing stock solutions of polycationic biomaterial(s), such as gelatin, dextran, de-acetylated form of chitin or cyclodextrin and polyanionic biomaterial(s), such as hyaluronic acid, alginate, casein, dextran sulfate, carrageenan, chondroitin sulfate, pectin, polygalacturonic acid, xanthan gum, heparin or their sodium or potassium or calcium salts or derivatives at room temperature (e.g. 20-25° C.). The stock solutions of the primary components are mixed together at desired weight ratio. The mixture of the primary constituents is washed with organic solvents having low-surface tension, such as methanol, ethanol, tert-butenol, acetone or hexane to replace the water. Then the organic solvent is evaporated by quick drying over hot surface to produce nano-fibrous polycationic complex having a diameter in a range of 20-200 nanometer. The polycationic and polyanionic biomaterials can be mixed in a weight ratio ranging from 8:2 to 2:8. Polycationic biomaterials, such as gelatin, dextran, de-acetylated form of chitin or cyclodextrin or their derivatives may be obtained from variety of commercial sources including but not limited to sources, such as Sigma-Aldrich (MO, USA), Hi-Media (Mumbai, India) and Loba Chemie (Mumbai, India). Gelatin, dextran, de-acetylated form of chitin or cyclodextrin or their derivatives may be employed as polycation, for example derivatives in which aceylation percentage is altered or the polymer length is reduced for the purpose of altering the solubility or other physicochemical property. Natural polyanions such as casein, hyaluronic acid, alginate, dextran sulfate, carrageenan, chondroitin sulfate, pectin, polygalacturonic acid, xanthan gum, heparin or their sodium or potassium or calcium salts can be used. Antimicrobials agents, growth factors, debraiding agents etc. may also be added with the prepared nano-fibrous polyelectrolyte complex to develop would dressing material with hemostatic property. Thus, it is to be well understood that some features mentioned herein may be used in combination with any other features of the prior art. However, the specific embodiments disclosed herein are actually the preferred embodiments of the present invention. These features are indispensable or essential.

The present disclosure encompasses preparation of a composition (nano-fibrous polyelectrolyte complex powder) which has a diameter of less than 100 nanometer and can quickly clot the blood in less than 20 seconds in case of any kind of fatal injuries ranging from superficial to deep wounds and minor to severe injuries and almost instantaneously in cases rise due to medical reasons. In cases of traumatic injuries caused due to gunshots, knife stabbing, accidental trauma, automobile accidents etc., the present disclosure facilitates an opportunity for the victims to reach to the point of care without losing fatal amount of blood. The use of such haemorrhage controlling agent (hemostatic agent) as described herein would be highly beneficial in case of injuries which causes severe bleeding.

The disclosed composition (nano-fibrous polyelectrolyte complex) is biocompatible, biodegradable and, when applied to the bleeding surface (e.g. wound), it absorbs a substantial amount of fluid and leads to blood clotting without causing undue desiccation in the wound site. The polyelectrolytes are macromolecules which exhibit a net positive or negative charge when dissolved in a polar solvent like water at a particular pH. When oppositely charged polyelectrolytes come into contact with each other, they form polyelectrolyte complex or otherwise known as polysalts. The driving force for the formation of polyelectrolyte complex is the entropy and strong electrostatic attraction between the oppositely charged polymers. When the negatively charged group comes into proximity with the positively charged group, they start attracting each other and an ionically cross-linked material forms. Cross link refers to the bonds that link one polymer chain to another polymer. In the presence of some cross-linking agents the negative functional groups from the same or different chain are attracted towards the positive charged functional groups. This cross-linking phenomenon also depends on the pH. For example, in the present embodiment the nano-fibres can only be formed if the pH of the complex is maintained between a range that is suitable for the nano-fibre formation. Beyond a certain pH value, fiber formation become less and more of particle formation takes place. When this cross-linked compound comes into contact with blood, it compels the blood cells to bind or get trapped onto the surface of the substrate helping them to create a mesh which leads to a strong patch formation.

As per one of the embodiments, two stock solutions of biomaterials are mixed together. Polycation, such as de-acetylated form of chitin and polyanions, such as casein are used as the primary components to form the nano-fibrous polyelectrolyte complex. The formation of the complex is spontaneous and accompanied by the release of counter ions. The processing is completely aqueous based and does not require any toxic solvents.

Once the polyelectrolyte complex is formed, a water replacing agent (desolvating agent) is introduced in the very next step of the fabrication process. This water replacing agent plays a key role in developing the dry nano-fibrous polyelectrolyte complex powder. It allows the nano-fibers not to get clumped together to form agglomeration in the preferred embodiment. When the water molecules are fully replaced by the said agent and heated up, the aforesaid agent evaporates, leaving behind nano-pores and fibrous structure, which in turn increases the surface-to-volume ratio of the nano-fibres. This increased surface-to-volume ratio leads to higher absorption property of the nano-fibrous samples. Herein, the prepared polyelectrolyte complex (composition of the present disclosure) is washed with organic solvents (desolvating agent) with low surface tension such as methanol, ethanol, butanol, acetone or hexane to replace the water molecules, which later helps in creating pores and fibrous structure during the drying process. As per the present disclosure, tertiary butanol provides the best result and the resulting final fibrous complex exhibits a nano-structure with a fiber diameter of less than 200 nm.

Polycationic biomaterial including, but not limited to, gelatin, dextran, de-acetylated form of chitin, cyclodextrin or poly-L-Lysine can be used. In the present disclosure, de-acetylated form of chitin (chitosan) gives the best result.

Polyanionic biomaterials including, but not limited to, casein, hyaluronic acid, alginate, dextran sulfate, carrageenan, chondroitin sulfate, pectin, polygalacturonic acid, xanthan gum, heparin or their sodium or potassium or calcium salts can be used. In the present disclosure, casein has been used and it gives the best result.

The disclosed composition (nano-fibrous polyelectrolyte complex) can be made in powder form, gel form or in liquid form. Furthermore, the present disclosure is not limited to polyelectrolyte complex only, composed of polysaccharide and protein, moreover as other hemostats such as biological hemostats, bioactive glasses, molecular sieve materials, thrombin, fibrin, other similar materials or combinations of the aforesaid with the present embodiment are within the scope of the present disclosure.

Any other clay or other clotting agents or materials of some embodiments can be added with the current embodiment or may be used in conjugation, that could result in improvement of the efficacy of the composition of the present disclosure. Some of the embodiments may involve, adding or integrating of several materials into the present disclosure for maintaining or improving the antiseptic environment at the injured area. For example, anti-inflammatory agents, anti-fungal agents, antibiotics, anti-histamines, anti-microbial agents, silver ions or compound containing copper, combination of the aforesaid and similar other materials can be used. Also, some different materials can be merged with the present embodiment to incorporate a pain relief property to it. Biological hemostatic materials, such as human serum albumin, bovine Thrombin, calcium, human Thrombin (hThrombin), rhThrombin, factor XIII, factor VIIa, recombinant Factor XIII (rFactor XIII), prostaglandin-2a, thromboxane A2, epidermal growth factor, tumor necrosis factor (TNF), platelet derived growth factor, TNF-alpha, transforming growth factor (TGF), Von Willebrand factor, TGF-alpha, TGF-beta, fibroblast growth factor, nerve growth factor, insulin like growth factor, keratinocyte growth factor, penicillin, methicillin, ampicillin, amoxycillin, clavulanic acid, clavamox, aztrenam, streptomycin, imipenem, kanamycin, bacitracin, tobramycin, vancomycin, polymyxin, gentamicin, clindamycin, erythromycin, amphotericin, rifampicin, nystatin, tetracycline, doxycycline, chloramphenicol, fibrin, thrombin, ascorbic acid, rutin, tranexamic acid, combination of aforesaid or similar materials can be used with the present embodiment, to provide additional hemostatic functions, depending on the nature of the injury. Also, the plant derived agents which possess desirable effects at the trauma site can be used with the present embodiment such as, *Glycyrrhiza glabra, Thymus vulgaris, Alpinia officinarum, Vitis vinifera* and *Urtica dioica, Newbouldia laevis* (Leaves), *Annona senegalensis* (Leaves), *Cissampelos mucronata* (aerial part), *Cassytha filiformis* (aerial part) etc. can be used.

The material used in the present disclosure for water replacement, maybe also some other different alcohol. The water replacing material may be any other single alcohol, mixture of more than one alcohol, mixture of water and alcohol or a combination of the aforesaid. After repetitive washing with alcohol, the polyelectrolyte complex and alcohol suspension is dried at temperature within 70° C. to 110° C. which results in nano-fibrous material formation. The present disclosure is not restricted in this regard, moreover other nano-fibre preparation process with average fiber diameter within 100 nm are within the scope of the current embodiment.

Several types of materials with their different combinations may be used for arriving at the composition of the present disclosure. A material may be fibrous comprised of single or more fibre like threads or strings; mesh; gaze; woven or non-woven; absorbent or non-absorbent; tightly woven textile; porous or solid; sponge etc. In some embodiments, an amalgamation of the aforesaid can be used and they can be coupled with one another in different ways. In some embodiments, fibers can also be coated with one or more number of additive agents for improvement.

In some embodiments, several salts can be incorporated with the polyelectrolyte complex, such as, calcium chloride, sodium tri-polyphosphate, same type of salt or combination of the aforesaid.

Finally, to obtain the product different ways can be acquired. In some embodiments, dedicated driers can be used for drying, to get the final product. Dedicated drier refers to the driers available in the market, such as, spray drier, vacuum drier, drum drier or similar type of machine to solve the drying purpose or a combination of the aforesaid. In some embodiments, the final product may be achieved in two steps, drying the substrate, and post drying, converting the dried substrate into the desired form. Drying can be achieved in several ways: this includes raising the temperature of the surrounding air of the substrate so that the water replacing agent will completely evaporate. In some embodiments, substrate can be subjected to direct heat by any measure. In some embodiments, lyophilisation process can be utilised for drying purpose. The drying parameters, such as temperature, vacuum level, duration and/or pressure can be varied or adjusted to produce the product. Converting the dried substrate into the desired form can be achieved through different ways. In some embodiment, crushing or grinding of the dried substrate can be performed or similar kind of other methods can be acquired which does not appreciably depreciates the efficacy of the substrate. In some embodiment both heating and grinding can be done at the same time.

In the present disclosure, the revealed hemostatic agent has a very high absorption capability to one or more liquids like water, blood etc. In some embodiment, the substrate may possess absorption capacity of at least 4 to 10 times or even more of its initial dry weight.

For the justification of the ability of the composition described in the present disclosure, the composition was characterised using FESEM. Evaluation of blood clotting ability of the substrate described in the current embodiment was done using whole blood clotting assay. For ensuring the cell adhesion capability of the substrate in the current embodiment, blood with the substrate was interrogated by using FESEM. The present disclosure also includes the ability of the substrate to withstand the blood pressure at the injury site. It refers that the substrate will remain there at the wounded area after applying and will not wash away with the blood flow. It will create a stiff patch over there resulting in no further bleeding.

The disclosed nano-fibrous polyelectrolyte complex typically can be placed in suitable sealed packaging (e.g. pouch or a vial made of suitable materials, or a kit containing such packaging and optionally contains printed instructions) and subjected to sterilization before being further packaged if need be with printed instructions describing the proper use of the material or kit in the treatment of haemorrhage. Suitable sterilization methods include ionizing radiation (e.g. gamma radiation) or ethanol treatment.

The disclosed nano-fibrous polyelectrolyte complex may be applied directly (e.g. for clean wounds) or as a part of a multi-step treatment regimen (e.g. for infected wound). The multi-step treatment regimen may include or be followed by a cleaning and disinfection step followed by the application of the disclosed nano-fibrous polyelectrolyte complex.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm. In another embodiment, the composition is in form of nanofibers having a diameter in a range of 30-175 nm. In yet another embodiment, the composition is in form of nanofibers having a diameter in a range of 20-150 nm. In an alternate embodiment, the composition is in form of nanofibers having a diameter in a range of 20-100 nm. In a still another embodiment, the composition is in form of nanofibers having a diameter in a range of 20-80 nm.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and wherein the polyanionic component comprising casein or derivatives thereof has casein in a weight percentage range of 20-80% with respect to the composition. In another embodiment, the polyanionic component comprising casein or derivatives thereof has casein in a weight percentage range of 30-70% with respect to the composition.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and wherein the polycationic component comprising chitosan or derivatives thereof has chitosan in a weight percentage in a range of 20-80% with respect to the composition. In another embodiment, the polycationic component comprising chitosan or derivatives thereof has chitosan in a weight percentage in a range of 30-70% with respect to the composition.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and wherein the polyanionic component comprising casein or derivatives thereof and the polycationic component comprising chitosan or derivatives thereof have a weight ratio in a range of 2:8 to 8:2. In another embodiment, the polyanionic component comprising casein or derivatives thereof and the polycationic component comprising chitosan or derivatives thereof have a weight ratio in a range of 3:7 to 7:3.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and wherein the polyanionic component comprising casein or derivatives thereof further comprises at least one material selected from a group consisting of hyaluronic acid, alginate, dextran sulfate, carrageenan, chondroitin sulfate, pectin, polygalacturonic acid, xanthan gum, heparin, derivatives thereof, and combinations thereof.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and wherein the polycationic component comprising chitosan or derivatives thereof further comprises at least one material selected from a group consisting of gelatin, dextran, cyclodextrin, derivatives thereof, and combinations thereof.

In an embodiment of the present disclosure, there is provided a composition as described herein, wherein the polyanionic component comprising casein or derivatives thereof has casein in a weight percentage range of 20-80% with respect to the composition, and the polycationic component comprising chitosan or derivatives thereof has chitosan in a weight percentage in a range of 20-80% with respect to the composition, and the polyanionic component comprising casein or derivatives thereof further comprises at least one material selected from a group consisting of hyaluronic acid, alginate, dextran sulfate, carrageenan, chondroitin sulfate, pectin, polygalacturonic acid, xanthan gum, heparin, derivatives thereof, and combinations thereof, and the polycationic component comprising chitosan or derivatives thereof further comprises at least one material selected from a group consisting of gelatin, dextran, cyclodextrin, derivatives thereof, and combinations thereof.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and the composition further comprises at least one additive selected from a group consisting of antimicrobial agent, growth factor, debraiding agent, anti-histamine agent, anti-inflammatory agent, copper salts, silver salts, and combinations thereof.

In an embodiment of the present disclosure, there is provided a composition comprising: (a) a polyanionic component comprising casein or derivatives thereof; and (b) a polycationic component comprising chitosan or derivatives thereof, wherein the composition is in form of nanofibers having a diameter in a range of 20-200 nm, and the composition further comprises at least one additive selected from a group consisting of human serum albumin, bovine Thrombin, calcium, human Thrombin (hThrombin), rhThrombin, factor XIII, factor VIIa, recombinant Factor XIII (rFactor XIII), prostaglandin-2a, thromboxane A2, epidermal growth factor, tumor necrosis factor (TNF), platelet derived growth factor, TNF-alpha, transforming growth factor (TGF), Von Willebrand factor, TGF-alpha, TGF-beta, fibroblast growth factor, nerve growth factor, insulin like growth factor, keratinocyte growth factor, penicillin, methicillin, ampicillin, amoxycillin, clavulanic acid, clavamox, aztrenam, streptomycin, imipenem, kanamycin, bacitracin, Tobramycin, vancomycin, polymyxin, gentamicin, clindamycin, erythromycin, amphotericin, rifampicin, nystatin, tetracycline, doxycycline, chloramphenicol, fibrin, thrombin, ascorbic acid, rutin, tranexamic acid, *Glycyrrhiza glabra* extract, *Thymus vulgaris* extract, *Alpinia officinarum* extract, *Vitis vinifera* extract and *Urtica dioica* extract, *Newbouldia laevis* (Leaves) extract, *Annona senegalensis* (Leaves) extract, *Cissampelos mucronata* (aerial part) extract, *Cassytha filiformis* (aerial part) extract, and combinations thereof.

In an embodiment of the present disclosure, there is provided a process for preparing a composition comprising: (i) a polyanionic component comprising casein or derivatives thereof; and (ii) a polycationic component comprising chitosan or derivatives thereof, wherein the composition is in form of nanofibers having a diameter in a range of 20-200 nm, said process comprising: (a) contacting a first aqueous solution of the polyanionic component comprising casein or derivatives thereof with a second aqueous solution of the polycationic component comprising chitosan or derivatives thereof, to obtain an aqueous mixture; (b) processing the aqueous mixture to obtain suspended particles; (c) contacting the suspended particles with a desolvating agent, to obtain a suspension; and (d) drying the suspension to obtain the composition.

In an embodiment of the present disclosure, there is provided a process for preparing the composition as described herein, wherein the first aqueous solution comprises casein in a range of 0.5-4% w/v with respect to the first aqueous solution, and the second aqueous solution comprises chitosan in a range of 0.5-3.5% w/v with respect to the second aqueous solution. In another embodiment, the first aqueous solution comprises casein in a range of 1-3.5% w/v with respect to the first aqueous solution, and the second aqueous solution comprises chitosan in a range of 1-3% w/v with respect to the second aqueous solution.

In an embodiment of the present disclosure, there is provided a process for preparing the composition as described herein, wherein the desolvating agent is selected from a group consisting of tertiary butanol, ethanol, acetone, and combinations thereof.

In an embodiment of the present disclosure, there is provided a process for preparing the composition as described herein, wherein the first aqueous solution and the second aqueous solution is prepared in water.

In an embodiment of the present disclosure, there is provided a process for preparing the composition as described herein, wherein the suspended particles has a pH in a range of 4 to 10.

In an embodiment of the present disclosure, there is provided a process for preparing the composition as described herein, wherein processing the aqeous mixture comprises the step of homogenization.

In an embodiment of the present disclosure, there is provided a process for preparing the composition as described herein, wherein contacting the first aqueous solution of the polyanionic component comprising casein or derivatives thereof with a second aqueous solution of the polycationic component comprising chitosan or derivatives thereof is done in a drop-wise manner.

In an embodiment of the present disclosure, there is provided a process for preparing the composition as described herein, wherein the polyanionic component comprising casein or derivatives thereof further comprises at least one material selected from a group consisting of hyaluronic acid, alginate, dextran sulfate, carrageenan, chondroitin sulfate, pectin, polygalacturonic acid, xanthan gum, heparin, derivatives thereof, and combinations thereof, and the polycationic component comprising chitosan or derivatives thereof further comprises at least one material selected from a group consisting of gelatin, dextran, cyclodextrin, derivatives thereof, and combinations thereof.

In an embodiment of the present disclosure, there is provided a process for preparing the composition as described herein, wherein the process further comprises adding at least one additive selected from a group consisting of antimicrobial agent, growth factor, debraiding agent, anti-histamine agent, anti-inflammatory agent, copper salts, silver salts, and combinations thereof.

In an embodiment of the present disclosure, there is provided a process for preparing the composition as described herein, wherein the process further comprises adding at least one additive selected from a group consisting of human serum albumin, bovine Thrombin, calcium, human Thrombin (hThrombin), rhThrombin, factor XIII, factor VIIa, recombinant Factor XIII (rFactor XIII), prostaglandin-2a, thromboxane A2, epidermal growth factor, tumor necrosis factor (TNF), platelet derived growth factor, TNF-alpha, transforming growth factor (TGF), Von Willebrand factor, TGF-alpha, TGF-beta, fibroblast growth factor, nerve growth factor, insulin like growth factor, keratinocyte growth factor, penicillin, methicillin, ampicillin, amoxycillin, clavulanic acid, clavamox, aztrenam, streptomycin, imipenem, kanamycin, bacitracin, tobramycin, vancomycin, polymyxin, gentamicin, clindamycin, erythromycin, amphotericin, rifampicin, nystatin, tetracycline, doxycycline, chloramphenicol, fibrin, thrombin, ascorbic acid, rutin, tranexamic acid, *Glycyrrhiza glabra* extract, *Thymus vulgaris* extract, *Alpinia officinarum* extract, *Vitis vinifera* extract and *Urtica dioica* extract, *Newbouldia laevis* (Leaves) extract, *Annona senegalensis* (Leaves) extract, *Cissampelos mucronata* (aerial part) extract, *Cassytha filiformis* (aerial part) extract, and combinations thereof.

In an embodiment of the present disclosure, there is provided a hemostatic article comprising a composition, said composition comprising: (a) a polyanionic component comprising casein or derivatives thereof; and (b) a polycationic component comprising chitosan or derivatives thereof, wherein the composition is in form of nanofibers having a diameter in a range of 20-200 nm. In another embodiment, the hemostatic article is in a form selected from a group consisting of bandage, spray, powder, paste, and foam.

In an embodiment of the present disclosure, there is provided a method for inhibiting loss of blood from a haemorrhaging site, said method comprising: (a) obtaining the composition as described herein or the hemostatic article as described herein; and (b) applying the composition or the hemostatic article to a haemorrhaging site for inhibiting loss of blood from the haemorrhaging site.

In an embodiment of the present disclosure, there is provided a method for inhibiting loss of blood from a haemorrhaging site, said method comprising: (a) obtaining the composition as described herein or the hemostatic article as described herein; and (b) applying the composition or the hemostatic article to a haemorrhaging site for inhibiting loss of blood from the haemorrhaging site, wherein the composition inhibits loss of blood in less than 50 seconds of application. In another embodiment, the composition inhibits loss of blood in 12-30 seconds of application.

In an embodiment of the present disclosure, there is provided a method for inhibiting loss of blood from a haemorrhaging site, said method comprising: (a) obtaining the composition as described herein; and (b) applying the composition to a haemorrhaging site for inhibiting loss of blood from the haemorrhaging site.

In an embodiment of the present disclosure, there is provided a method for inhibiting loss of blood from a haemorrhaging site, said method comprising: (a) obtaining the hemostatic article as described herein; and (b) applying the hemostatic article to the haemorrhaging site for inhibiting loss of blood from the haemorrhaging site.

In an embodiment of the present disclosure, there is provided a use of the composition comprising: (i) a polyanionic component comprising casein or derivatives thereof; and (ii) a polycationic component comprising chitosan or derivatives thereof, wherein the composition is in form of nanofibers having a diameter in a range of 20-200 nm for inhibiting loss of blood from a haemorrhaging site.

In an embodiment of the present disclosure, there is provided a use of the hemostatic article comprising a composition, said composition comprising: (i) a polyanionic component comprising casein or derivatives thereof; and (ii) a polycationic component comprising chitosan or derivatives thereof, wherein the composition is in form of nanofibers having a diameter in a range of 20-200 nm for inhibiting loss of blood from a haemorrhaging site.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The present section exemplifies the various embodiments of the present disclosure. It categorically provides the advantages of the embodiments.

Example 1

Preparation of the Composition as Disclosed in the Present Disclosure

Chitosan (polycationic component) and casein (polyanionic component) was used to prepare the composition as disclosed in the present disclosure. Chitosan (>75% deacetylation, Molecular weight 3800-20000 gmol$^{-1}$) and casein (Molecular weight 4, 23,644 gmol$^{-1}$) were obtained from Himedia Laboratories. Chitosan solution varying from 0.5% to 3.5% (w/v) was prepared in water (second aqueous solution), and casein solution varying from 0.5% to 4% (w/v) was prepared in water (first aqueous solution). The second aqueous solution was then added to the first aqueous solution to obtain an aqueous mixture. For the experimentation purpose, three different ratios of mixture were prepared. The prepared samples are referred to as: CA30CH70 (casein:chitosan in a weight ratio of 30:70); CA50CH50 (casein:chitosan in a weight ratio of 50:50); and CA70CH30 (casein:chitosan in a weight ratio of 70:30). The details of the three compositions of the aforesaid samples is described in the Table 1 below.

The aqueous mixture that were obtained for three different ratios were independently processed. The processing involved homogenization process, and adjusting the pH in the range between 6-10 to obtain suspended particles. The suspended particles were washed with alcohol in a repeated manner to ensure the absence of any water molecules in the particles. The particles were further dissolved in a desolvating agent (or any liquid having a boiling point lower than water) to obtain a suspension. In order to dry the suspension, manual drying procedure was adopted. The suspension was sprayed on a hot plate or an heated aluminium foil (50° C.–80° C.) in a well-ventilated area to dry the suspension. After the drying step, the composition as disclosed in the present disclosure is obtained in a powder form which can be collected in a tube for further studies and/or applications. The flakes of the composition were further made finer by using a vibrator. The process as disclosed led to the obtainment of composition in form of three different samples; Sample 1 (CA30CH70), Sample 2 (CA50CH50), and Sample 3 (CA70CH30) as depicted in Table 1. The process for obtaining the composition as per the present disclosure is outlined in FIG. 1.

As part of the present disclosure, Samples 4-6 were also prepared by tweaking certain steps as mentioned in the above paragraph. Same process steps were followed till the step of obtaining the suspended particles in the different samples having different ratios of chitosan and casein as mentioned in Table 1. The suspended particles were not washed with alcohol and subsequently were not dissolved in any desolvating agent. The suspended particles were independently dried over the hot plate, to obtain Sample 4 (CA30CH70_film), Sample 5 (CA50CH50_film), and Sample 6 (CA70CH30_film). The samples 4-6 were in form as films as against samples 1-3 which were in form of fine powder. The samples 4-6 were composed of films having a thickness of about 10 microns.

TABLE 1

| Sample No. | Sample name | Casein percentage (v/v %) | Chitosan percentage (v/v %) |
|---|---|---|---|
| 1 | CA30CH70 | 30 | 70 |
| 2 | CA50CH50 | 50 | 50 |
| 3 | CA70CH30 | 70 | 30 |
| 4 | CA30CH70_film | 30 | 70 |
| 5 | CA50CH50_film | 50 | 50 |
| 6 | CA70CH30_film | 70 | 30 |

Example 2

Field Emission Scanning Electron Microscope (FESEM) Imaging Studies

Figure 2:
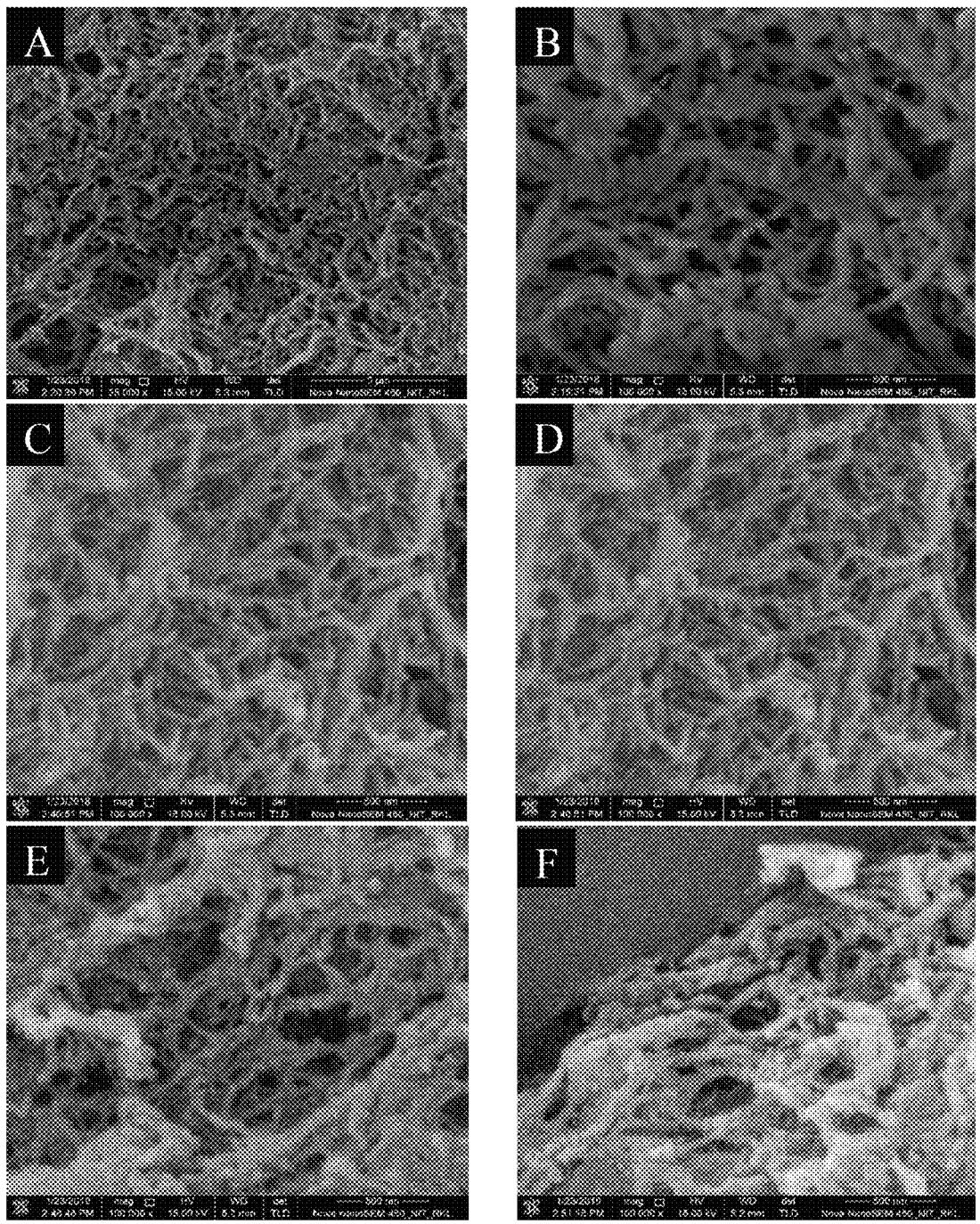
FIG. 2 illustrates the FE-SEM images of composition of the present disclosure having casein and chitosan in 30:70 weight ratio (CA30CH70 PEC powder) (A, B), casein and chitosan 50:50 weight ratio (CA50CH50 powder) (C, D) and casein and chitosan 70:30 weight ratio (CA70CH30 powder) (E, F) at lower and higher magnification respectively, indicating diameter of the nanofibers, in accordance with an embodiment of the present disclosure.

In order to analyse the nano-level structures of the composition of Samples 1-3 as obtained from Example 1, FESEM imaging of different samples was performed. In the FESEM imaging, it was observed that all the samples have a nano-fibrous structure with a fiber diameter ranging from 20 to 200 nm. FIG. 2 shows the nano-fibrous structure of the composition as obtained herein. FIGS. 2A and 2B show the nanofibers for the composition represented by Sample 1 (CA30CH70). FIGS. 2C and 2D show the nanofibers for the composition represented by Sample 2 (CA50CH50). FIGS. 2E and 2F show the nanofibers for the composition represented by Sample 3 (CA70CH30). It can be concluded that all the Samples 1-3 show the nanofibers having diameted in a range of 20-200 nm as per the present disclosure.

Example 3

Zeta Potential Analysis

Figure 3:
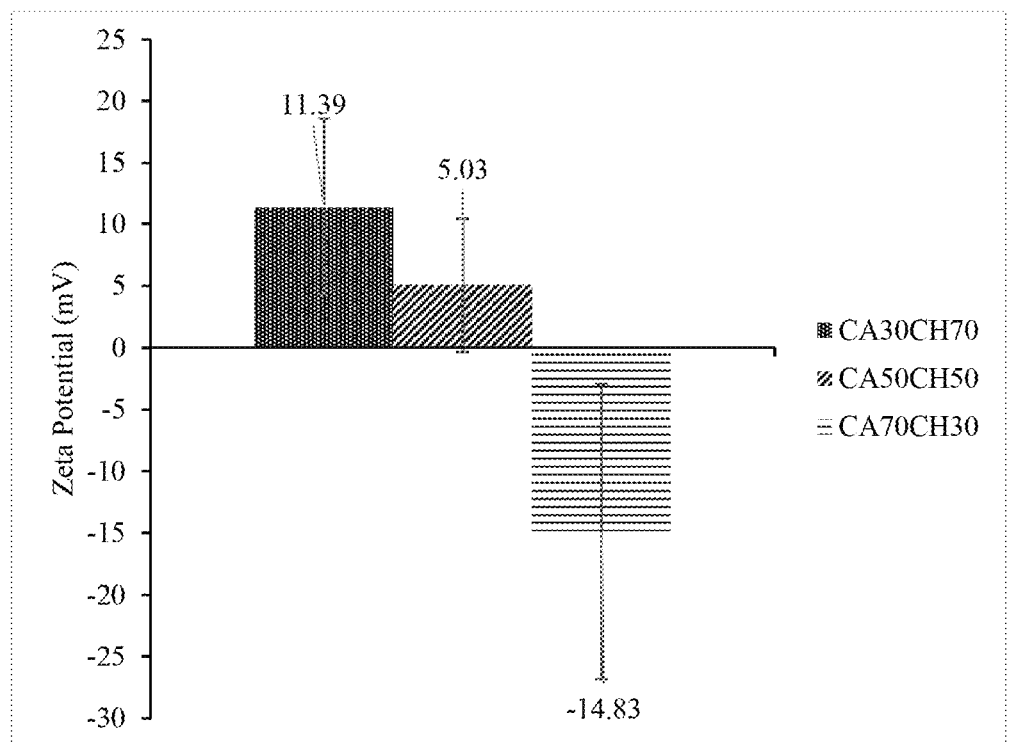
FIG. 3 illustrates the surface charges for CA30CH70, CA50CH50 & CA70CH30, in accordance with an embodiment of the present disclosure.

Measurement of Zeta potential values provides a measurable information about the charge present on the surface of the nanofibers of the composition. FIG. 3 represents the zeta potentials of nanofibres of the composition at different compositional ratios as described in Example 1. Sample 1 (nano-fibres composed of casein 30% with chitosan 70%) shows a zeta potential of 11.39±7.19 mV. This charge continues to decrease with the decrement of chitosan amount in the PEC. The PEC nanofibres composed of 70% casein show a zeta potential of −14.83±11.95 mV. The zeta potential measurement suggests that the surface charge of the nanofibers is correlated with their composition. The surface charge increases with increase in concentration of chitosan. FIG. 3 depicts surface charges for Sample 1 (CA30CH70), Sample 2 (CA50CH50), and Sample 3 (CA70CH30).

Example 4

Whole Blood Clotting Assay

The blood clotting ability of the composition (Samples 1-6) described in the Example 1 was measured through whole blood clotting assay. 200 μL of blood was taken into a microcentrifuge tube (eppendorf tube), and to that 20 μL of 0.2 M calcium chloride solution and respective samples, were added simultaneously. This procedure was repeated for each of the samples. Clotting of the blood was ensured by shaking the tube to see whether the blood has any movement or not, and the time was noted. For comparison with the samples, Celox™ was taken as a reference. Respective clotting times of different samples are mentioned in Table 2.

TABLE 2

| Sample No. | Samples | Blood Clotting time (Seconds) |
|---|---|---|
| 1 | CA30CH70 | 15 ± 2 |
| 2 | CA50CH50 | 14 ± 3 |
| 3 | CA70CH30 | 13 ± 3 |
| 4 | CA30CH70_film | 189 ± 6 |
| 5 | CA50CH50_film | 212 ± 3 |
| 6 | CA70CH30_film | 233 ± 5 |
| — | Celox ™ (30%) | 98 ± 6 |
| — | Pure Blood | 278 ± 14 |

From the Table 2 it can be observed that the Samples 1-3 displayed lesser clotting time as compared to a commercial product (Celox™). Further, the Samples 1-3 also displayed lesser clotting time of 15 seconds, 14 seconds, and 13 seconds respectively, as compared to the samples 4-6 (189 seconds, 212 seconds, 233 seconds) which are in form of film and has different processing steps as described in Example 1. Therefore, it can be appreciated that the nanofibers morphology (diameter of nanofibers in a range of 20-200 nm as shown in Example 2) of the Samples 1-3 is crucial in achieving lesser clotting time as compared to the Samples 4-6 which lack nanofibers and are present in form of films.

Example 5

Cell Adhesion Test

Figure 4:
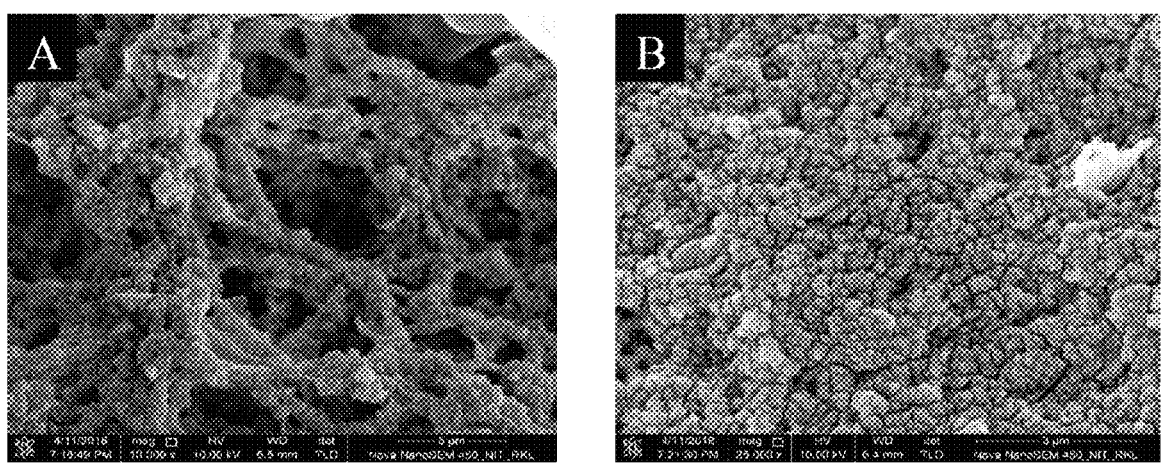
FIG. 4 illustrates the FE-SEM images of blood clots, treated with PEC powder samples of CA30CH70 (A, B), CA50CH50 (C, D), CA70CH30 (E, F) & Celox (G, H) at lower and higher magnification respectively, in accordance with an embodiment of the present disclosure.
Figure 4:
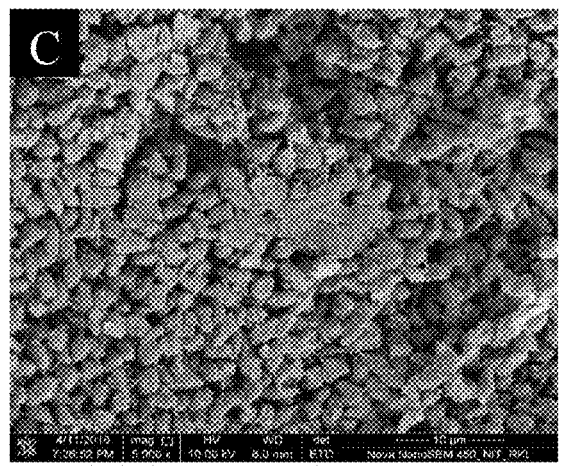
Figure 4:
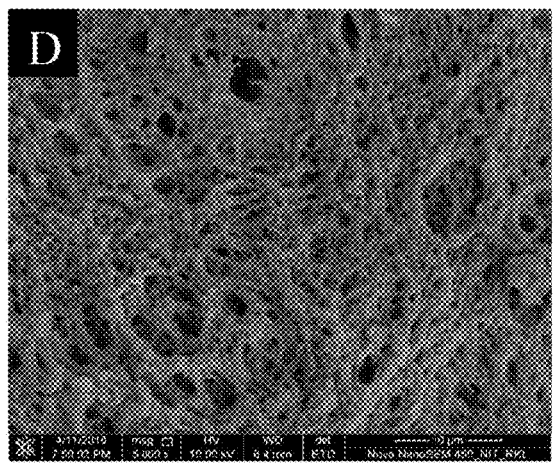
Figure 4:
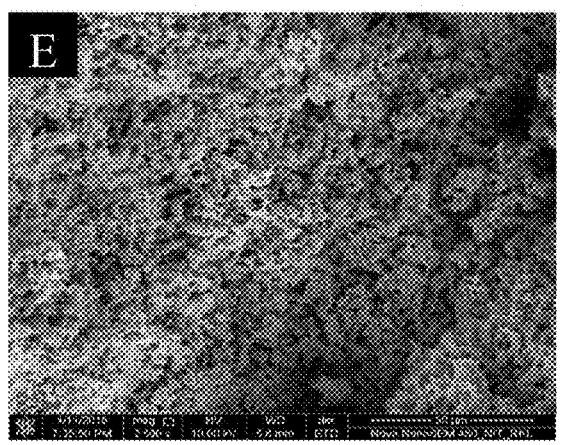
Figure 4:
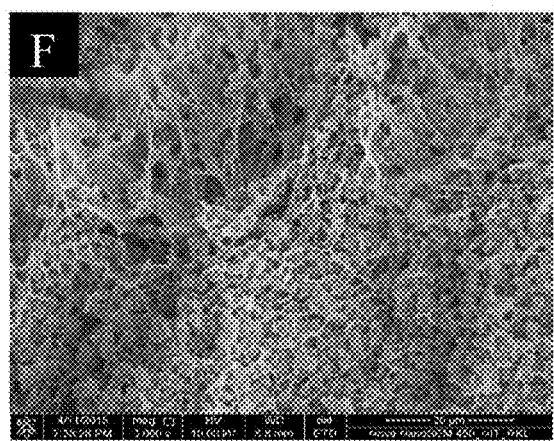

For studying the cell adhesion qualities, Samples 1-3 were used to clot blood samples as explained in Example 4. After the whole blood samples form a clot, the clot samples were fixed by dipping them in formalin for 12 hrs. After that, the fixed clots were taken out and dipped into tertiary butyl alcohol for 12 hrs. Then the samples were dried in vacuum drier. Clot samples were then studied through FESEM imaging. FIG. 4 shows the FESEM imaging test results.

FIG. 4 depicts FE-SEM images of blood clots obtained using Sample 1—CA30CH70 (A, B), Sample 2—CA50CH50 (C, D), and Sample 3—CA70CH30 (E, F), and Celox™ (G, H) at lower and higher magnification respectively. These figures showed that all samples promoted cell adhesion irrespective of their compositions and surface charge.

Example 6

Lactate Dehydrogenase (LDH) Test

Adhesion of platelets on the surface of the nanofibers of the composition represented by Samples 1-3 was quantified through the amount of LDH released at the time of cell lysis. The cells were lysed with 1% tritonX100 solution. The concept behind this test was that every cell contains LDH, so higher LDH activity in the solution means, the more number of platelets have adhered to the fiber's surface.

Figure 5:
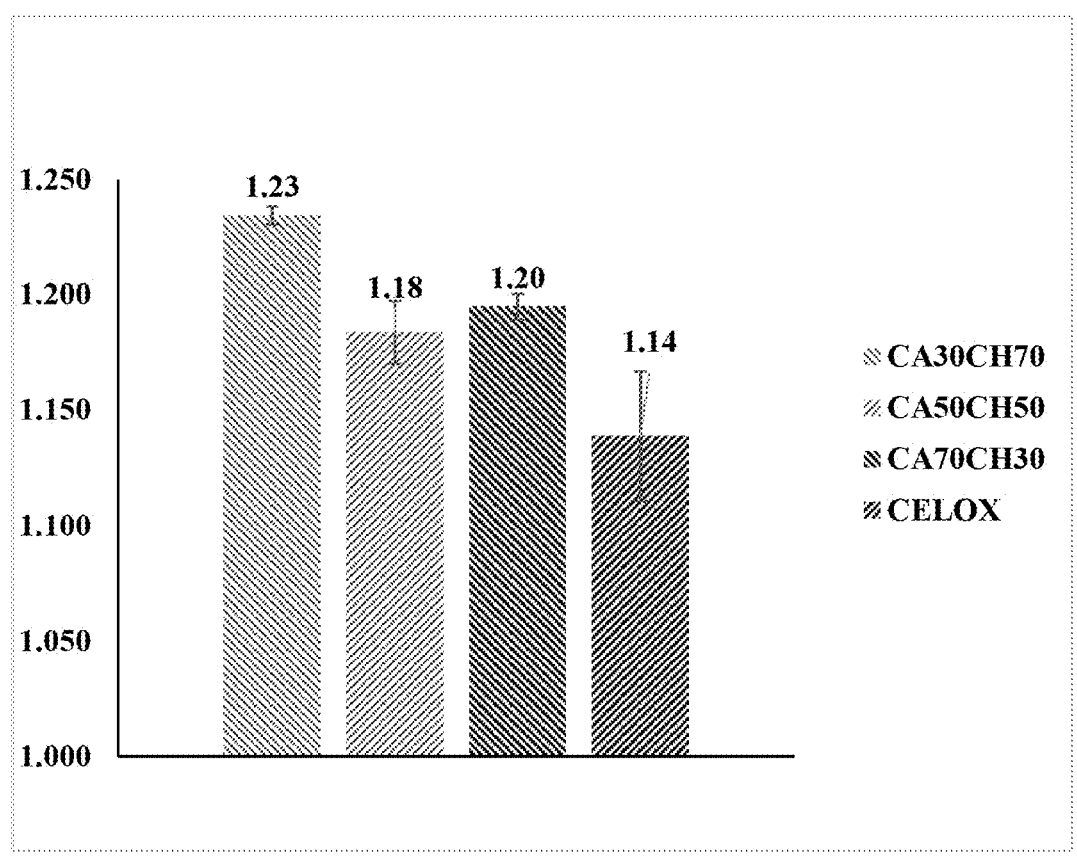
FIG. 5 illustrates the LDH activity for CA30CH70, CA50CH50, CA70CH30 & Celox, in accordance with an embodiment of the present disclosure.

FIG. 5 depicts a graph representing the LDH quantity after performing the LDH test. From the graph (FIG. 5), it is clear that Samples 1-3 have significantly higher cell adhesion capability and there were more number of platelets attached to their surface compared to the commercial product. This may have happened due to the surface charge of the samples. The surface charge plays an important role in cell adhesion, as it influences the platelets and the plasma proteins. The charged surface also helps in forming the prothrombinase complex (activated F-V and F-X) and the intrinsic tenase complex (activated F-VIII and F-IX), that leads to blood clotting. Therefore, this example again proves that the composition of the present disclosure represented in form of Samples 1-3 are favourable as hemostatic agents.

Example 7

Haemolysis Assay

Haemolytic property of the Samples 1-3 was performed to evaluate whether the samples are compatible with the blood cells or not. To perform this test, 0.9% NaCl solution was prepared. The anti-coagulated blood was diluted by adding the NaCl solution at 4:5 ratio. Equal amount of samples were placed in the 15 ml polypropylene tubes with 6 ml of NaCl solution and kept at 37° C. for 30 minutes. After incubation, in each of the polypropylene tubes, 0.5 ml of diluted blood was added and kept at 37° C. for 2 hours. Positive and negative controls were also prepared. Positive control was made by adding 6 ml NaCl solution, 0.5 ml diluted blood and 0.01 M HCl solution. Negative control was made by adding 6 ml NaCl solution and 0.5 ml diluted blood. After 2 hours of incubation, all the samples were centrifuged at 2000 g for 20 minutes. At last, OD values of the supernatants were taken at 540 nm. The test was performed in triplicate. The measured hemolysis percentage data for Samples 1, 2 and 3 are mentioned in Table 3 below. All the samples exhibited significantly lower hemolysis compared to Celox™. Therefore, it can be appreciated that the composition as per the present disclosure is safer to use and is not harmful to the red blood cells and are haemo-compatible.

TABLE 3

| Sample No. | Sample Name | Hemolysis (%) |
|---|---|---|
| 1 | CA30CH70 | 1.49 ± 0.34 |
| 2 | CA50CH50 | 1.82 ± 0.13 |
| 3 | CA70CH30 | 3.06 ± 0.30 |
| — | Celox ™ | 10.00 ± 2.80 |

Example 8

Prothrombin Time Test

Prothrombin test (PT) is an indicator to show whether the samples have any extrinsic pathway of the coagulation cascade or not. It signifies the duration in which the extrinsic pathway is initiated. A shortened PT indicates an improved clotting efficiency. This PT test can also be called as INR (International Normalized Ratio) test. This INR test actually standardizes the results obtained from prothrombin time test without considering the test method.

Prothrombin, or F-II, is one of the real-time clotting factors. PT test is very important in order to check if 5 different coagulation factors (F-I, F-II, F-V, F-VII, and F-X) are present in the blood or not and they are properly working or not.

Figure 6:
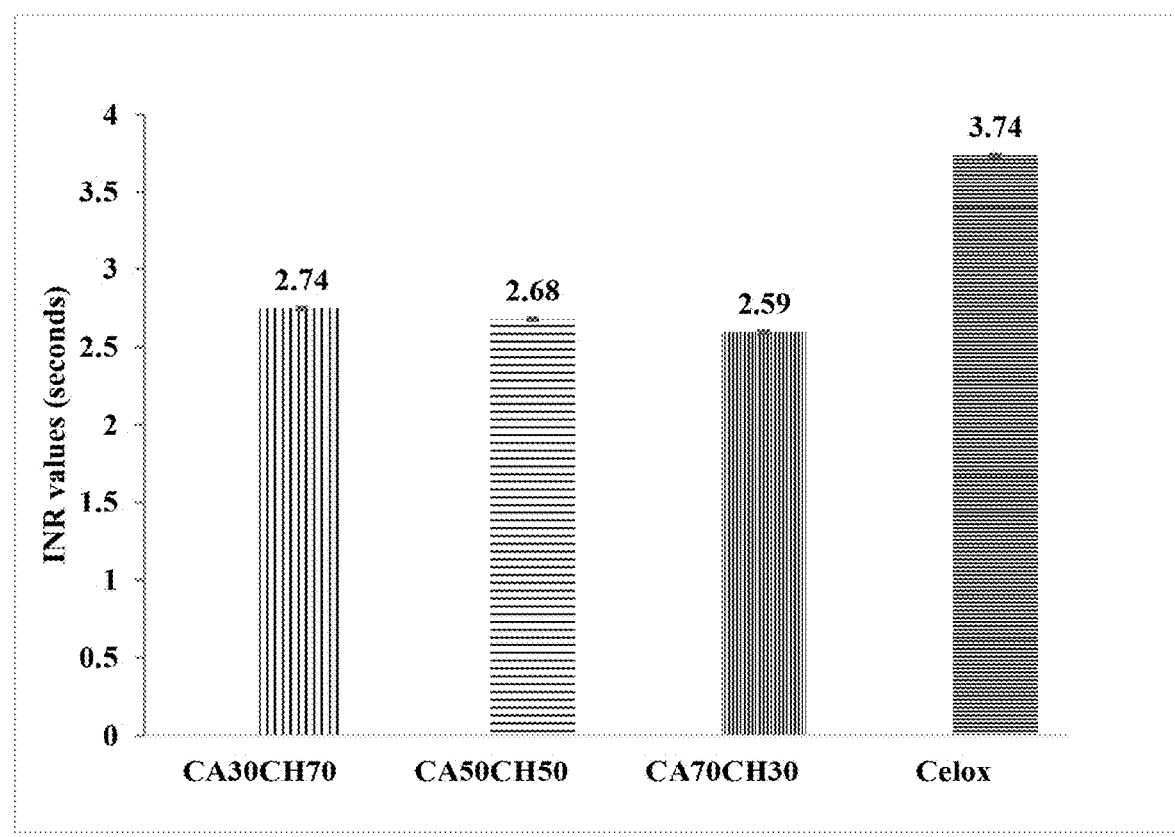
FIG. 6 illustrates the prothrombin time for CA30CH70, CA50CH50, CA70CH30 & Celox, in accordance with an embodiment of the present disclosure.

Normally the PT value lies between 2 to 3. If it is below 2 then it means the blood has a high clotting tendency and if it is above 3 then it denotes that the blood has a delayed clotting tendency. FIG. 6 depicts prothrombin test for Sample 1 (CA30CH70), Sample 2 (CA50CH50), and Sample 3 (CA70CH30), and Celox. It can be observed that the values of INR is between 2 and 3 in case of all the Samples 1-3. Therefore, it can be appreciated that the composition of the present disclosure initiates the clotting of the blood in a natural manner.

ADVANTAGES OF THE PRESENT DISCLOSURE

The present disclosure discloses a composition comprising a polyanionic component comprising casein or derivatives thereof; and a polycationic component comprising chitosan or derivatives thereof, wherein the composition is in the form of nanofibers having a diameter in a range of 20-200 nm. The composition as described herein is fast acting and shows almost instantaneous action in inhibiting loss of blood. The composition exhibits high levels of blood clotting as depicted by the assays. The composition is biodegradable and environment friendly. Further, there is no visible side effect due to the use of biopolymers like casein and chitosan. The process employed for preparing the composition of the present disclosure is easy and scalable and provides a high throughput result.

What is claimed is:
1. A composition comprising:
   a) a polyanionic component comprising casein or derivatives thereof; and
   b) a polycationic component comprising chitosan or derivatives thereof, wherein the composition is in the form of nanofibers having a diameter in a range of 20-100 nm.
2. The composition as claimed in claim 1, wherein the polyanionic component comprising casein or derivatives thereof has casein in a weight percentage range of 20-80% with respect to the composition.
3. The composition as claimed in claim 1, wherein the polycationic component comprising chitosan or derivatives thereof has chitosan in a weight percentage in a range of 20-80% with respect to the composition.
4. The composition as claimed in claim 1, wherein the polyanionic component comprising casein or derivatives thereof and the polycationic component comprising chitosan or derivatives thereof have a weight ratio in a range of 2:8 to 8:2.
5. The composition as claimed in claim 1, wherein the polyanionic component comprising casein or derivatives thereof further comprises at least one material selected from a group consisting of hyaluronic acid, alginate, dextran sulfate, carrageenan, chondroitin sulfate, pectin, polygalacturonic acid, xanthan gum, heparin, derivatives thereof, and combinations thereof.
6. The composition as claimed in claim 1, wherein the polycationic component comprising chitosan or derivatives thereof further comprises at least one material selected from a group consisting of gelatin, dextran, cyclodextrin, derivatives thereof, and combinations thereof.
7. A process for preparing the composition as claimed in claim 1, wherein the process comprises:
   a) contacting a first aqueous solution of the polyanionic component comprising casein or derivatives thereof with a second aqueous solution of the polycationic component comprising chitosan or derivatives thereof, to obtain an aqueous mixture;
   b) processing the aqueous mixture to obtain suspended particles;
   c) contacting the suspended particles with a desolvating agent, to obtain a suspension; and
   d) drying the suspension to obtain the composition.

8. The process as claimed in claim 7, wherein the first aqueous solution comprises casein in a range of 0.5-4% w/v with respect to the first aqueous solution, and the second aqueous solution comprises chitosan in a range of 0.5-3.5% w/v with respect to the second aqueous solution.

9. The process as claimed in claim 7, wherein the desolvating agent is selected from a group consisting of tertiary butanol, ethanol, acetone, and combinations thereof.

10. The process as claimed in claim 7, wherein the suspended particles has a pH in a range of 4 to 10.

11. The composition as claimed in claim 1, wherein the composition is for inhibiting loss of blood from a hemorrhaging site.

12. A hemostatic article comprising the composition as claimed in claim 1.

13. The hemostatic article as claimed in claim 12, wherein the hemostatic article is in a form selected from a group consisting of bandage, spray, powder, paste, and foam.

14. A method for inhibiting loss of blood from hemorrhaging site, said method comprising:
a) obtaining the composition as claimed in claim 1; and
b) applying the composition or the hemostatic article to the hemorrhaging site for inhibiting loss of blood from the hemorrhaging site.

15. A method for inhibiting loss of blood from a haemorrhaging site, comprising
a) obtaining the hemostatic article as claimed in claim 13; and
b) applying the composition or the hemostatic article to the hemorrhaging site for inhibiting loss of blood from the hemorrhaging site.

16. A method for inducing blood clotting in a wound comprising applying the composition as claimed in claim 1 to the wound, thereby inducing blood clotting in the wound.

* * * * *